US00PP13835P39

(12) United States Plant Patent
Olesen et al.

(10) Patent No.: US PP13,835 P3
(45) Date of Patent: May 20, 2003

(54) FLORIBUNDA ROSE PLANT NAMED 'POULROHILL'

(76) Inventors: L. Pernille Olesen, Hillerodvejen 49, Fredensborg DK-3480 (DK); Mogens Olesen, Hillerodvejen 49, Fredensborg DK-3480 (DK)

( * ) Notice: Subject to any disclaimer, the term of this patent is extended or adjusted under 35 U.S.C. 154(b) by 0 days.

(21) Appl. No.: 09/919,064
M

(22) Filed: Jul. 30, 2001

(65) Prior Publication Data

US 2003/0024020 P1 Jan. 30, 2003

(51) Int. Cl.[7] ..... A01H 5/00
(52) U.S. Cl. ..... Plt./148
(58) Field of Search ..... Plt./148, 141, 137

*Primary Examiner*—Bruce R. Campell
*Assistant Examiner*—June Hwu

(57) ABSTRACT

A new floribunda garden rose plant which has abundant, pink flowers and attractive foliage. This new and distinct variety has shown to be uniform and stable in the resulting generations from asexual propagation.

1 Drawing Sheet

SUMMARY OF THE INVENTION

Classification:
*Botanical.*—*Rosa hybrida* 'POULrohill'.
*Commercial.*—Floribunda.

The present invention constitutes a new and distinct variety of garden rose plant which originated from a controlled crossing between 'KORfalt', and 'DICjem', both unpatented varieties. The two parents were crossed during the summer of 1987 and the resulting seeds were planted in a controlled environment in Fredensborg, Denmark. The new variety is named 'POULrohill'.

The new rose may be distinguished from its seed parent, 'KORfalt', by the following combination of characteristics:

1. The seed parent is a yellow floribunda with red intonations on its outer petals, while 'POULrohill' is a pink floribunda.

The new variety may be distinguished from its pollen parent, 'DICjem' by the following combination of characteristics:

1. The pollen parent is a clear yellow flower and 'POULrohill' is a pink flower.
2. 'POULrohill' is a semi-double rose exhibiting 20–25 petals while 'DICjem' is a double rose averaging 35 petals.

The objective of the hybridization of this rose variety was to create a new and distinct variety for garden use with unique qualities, such as:

1. Uniform and abundant flowers;
2. Vigorous, but compact growth when propagated both as a budded rose and on its own roots;
3. Disease resistance.

This combination of qualities is not present in previously available commercial cultivars of this type and distinguish 'POULrohill' from all other varieties of which we are aware.

As part of their rose development program, L. Pernille Olesen and Mogens N. Olesen germinated the seeds from the aforementioned hybridization during winter 1987 and conducted evaluations on the resulting seedlings in a controlled environment in Fredensborg, Denmark.

'POULrohill' was selected in the spring 1998 by the inventors as a single plant from the progeny of the aforementioned hybridization.

Asexual reproduction of 'POULrohill' by traditional budding and rooted cuttings was first done by L. Pernille and Mogens N. Olesen in their nursery in Fredensborg, Denmark in August, in 1998. This initial and other subsequent asexual propagations conducted in controlled environments have demonstrated that the characteristics of 'POULrohill' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULrohill'. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Bare stems exhibiting thorns;
6. Leaves.

DETAILED DESCRIPTION OF THE VARIETY

The following is a description of 'POULrohill', as observed in its growth in a field nursery in Jackson County, Oreg. on plants aged 18 months. Color references are made using The Royal Horticultural Society (London, England) Colour Chart, 1995, except where common terms of color are used. For a comparison, several physical characteristics of the rose variety 'POULreb', a rose variety from the same inventors described and illustrated in U.S. Plant Pat. No. 12,534 filed Mar. 31, 1999 are compared to 'POULrohill' in Chart 1.

CHART 1

| | 'POULrohill' | 'POULreb' |
|---|---|---|
| Bud color, as sepals first divide | Red Group 50B. | Yellow Group 4c |

CHART 1-continued

| | 'POULrohill' | 'POULreb' |
|---|---|---|
| Color, upper surface, upon opening | Red Group 48 C and D. | Yellow Group 7B at base and Yellow Group 9D at tip |
| Petalage | 20–25 petals | 60–75 petals |

Parents:
*Seed parent.*—'KORfalt'.
*Pollen parent.*—'DICjem'.

FLOWER AND FLOWER BUD

Blooming habit: Continuous.
Flower bud:
*Size.*—Upon opening, 30 mm in length from base of receptacle to end of bud.
*Bud form.*—Long, pointed ovoid.
*Bud color.*—As sepals unfold, Red Group 50B. Red Group 52 B and C at ¼ opening.
*Sepals.*—Green Group 144B. Strong foliaceous appendages on three of the five sepals. Surfaces of sepals moderately pubescent. Stipitate glands are present on outer surface and edges of sepals. Sepals are 40 mm long and 10 to 14 mm wide.
*Receptacle.*—Surface: Slightly pubescent. Shape: Funnel. Size: Medium. 7 mm (h)×8 mm (w). Color: Yellow-Green Group 144B with inconsistent anthocyanin noted of Greyed-Purple Group 183B.
*Peduncle.*—Surface: Medium number of stipitate glands. Length: 50–70 mm average length. Color: Yellow-Green Group 144B–C with inconsistent anthocyanin noted of Greyed-Purple Group 183B. Strength: Strong.
*Borne.*—Singularly.
Flower bloom:
*Fragrance.*—Light and fresh.
*Duration.*—The blooms have a duration on the plant of approximately 10 to 12 days. As a cut flowers, the blooms last for approximately 5 days. Petals fall cleanly away from plant.
*Size.*—Medium. Average flower diameter is 65–70 mm when open.
*Form.*—Shape of flower when viewed from the side: Upon opening, upper part: Cupped. Upon opening, lower part: Flattened convex. Open flower, upper part: Convex. Open flower, lower part: Flattened convex.
*Petalage.*—Double. Average range: 20–25 petals under normal conditions with 3–5 petaloids.
Color:
*Upon opening, petals.*—Outermost petals: Outer side: Red-Purple Group 58 C and D. Inner Side: Red Group 48C and D. Innermost petals: Outer side: Red-Purple Group 58 C and D. Inner Side: Red Group 48C and D.
*Upon opening, basal petal spots.*—Outermost petals: Outer side: Green-Yellow Group 1B. Inner Side: Green-Yellow Group 1B. Innermost petals: Outer side: Green-Yellow Group 1B. Inner Side: Green-Yellow Group 1B.
*After opening, petals.*—Outermost petals: Outer side: Red Group 55 A and B. Inner Side: Red Group 55C and D. Innermost petals: Outer side: Red Group 55B. Inner Side: Red Group 55 C and D.
General tonality: On open flower, Red Group 55 C and D. No change in the general tonality at the end of the 6th day. Afterwards, general tonality is Red Group 56 A and B.
Petals:
*Petal reflex.*—Petal reflexes weakly.
*Petal edge.*—Entire and cuspidate. Base is acute.
*Shape.*—Round.
*Petaloids.*—Present. Quantity: 3–5. Size: Petaloids are 8 to 12 mm long and 10 mm wide. Color: Upper side is Red Group 55B; lower side is Red Group 55C.
*Thickness.*—Thick.
*Arrangement.*—Imbricated.
Reproductive organs:
*Pistils.*—Length: 7 mm. Quantity: 15 to 20.
*Pollen.*—Color: Greyed-Orange Group 163A. Quantity: Average.
*Anthers.*—Size: 3 to 4 mm long. Color: Greyed Group 160A. Quantity: 13–15.
*Filaments.*—Color: Yellow Group 13A.
*Stigmas.*—Superior in location to anthers. Color: Greyed-Yellow Group 160A.
*Styles.*—Color: White Group 155A with intonations of Greyed-Yellow Group 160A.
*Hips.*—None observed.

PLANT

Plant growth: Vigorous and bushy. When grown as a budded field grown plant on *Rosa multiflora* understock, the average height of the plant is 60–80 cm and the average width is 60–80 cm.
Stems:
*Color.*—Young wood: Yellow-Green Group 144B. Older wood: Yellow-Green Group 144B.
*Thorns.*—Incidence: Moderate. Size: Average length: 4 mm. Color: Greyed-Orange Group 164A to 165A. Shape: Concave.
*Surface.*—Young wood: Smooth. Older wood: Smooth.
Plant foliage: Normal number of leaflets on normal leaves in middle of the stem: 5 leaflets.
*Leaf size.*—Medium. 80 mm (l)×50 mm (w).
*Abundance.*—Very abundant.
*Color.*—Mature Foliage: Upper Leaf Surface: Green Group 137C. Lower Leaf Surface: Green Group 139D. Juvenile foliage: Upper Leaf Surface: Yellow-Green Group 144B. Lower Leaf Surface: Yellow-Green Group 144B. Anthocyanin intonation: Location: Leaf edges. Color: Red-Purple Group 60C.
Plant leaves and leaflets:
*Stipules.*—Size: Medium. 8 mm. Color: Yellow-Green Group 145C–D with Yellow-Green Group 145B at tips of stipules. Stipitate glands present along the leaf margin. Anthocyanin: Present on margins. Color: Greyed-Red Group 181A.
*Petiole.*—Length: 20–30 mm. Color: Yellow-Green Group 145B–D with intonations of Yellow-Green Group 144A. Underneath: Yellow-Green Group 145A–B. stipitate glands observed. Margins: Yellow-Green Group 144A. Anthocyanin: Present on margins. Color: Greyed-Red Group 181A.
*Rachis.*—Color: Yellow-Green Group 145B–D with intonations of Yellow-Green Group 144A. Underneath: Yellow-Green Group 145A–B. stipitate glands observed. Margins: Yellow-Green Group 144A.
*Leaflet.*—Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is glossy. Lower side of leaflet is matte. Leaflet is thick.

Disease resistance: 'POULrohill' is resistant to mildew, rust, black spot, and Botrytis under normal growing conditions in Jackson County, Oreg.

Winter hardiness: 'POULrohill' has been found to be resistant to damage from cold in USDA Zone 8 and USDA Zone 7.

We Claim:

1. A new and distinct variety of rose plant of the Floribunda rose class, substantially as herein illustrated and described as a distinct and novel rose variety due to its abundant, pink flowers, disease resistance, and extended period of bloom.

* * * * *

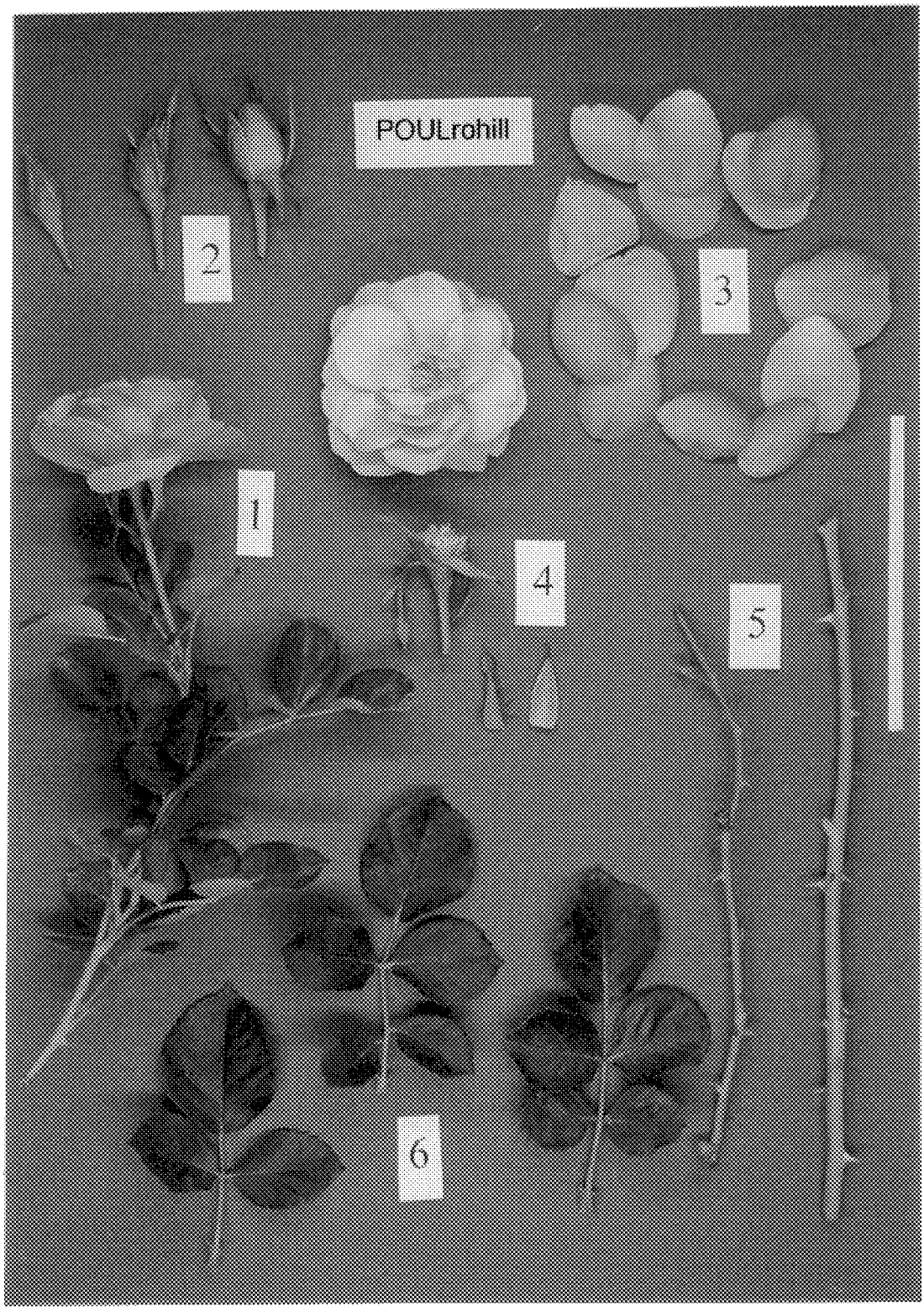
POULrohill
1
2
3
4
5
6